(12) United States Patent
Burkholz et al.

(10) Patent No.: US 11,147,957 B2
(45) Date of Patent: Oct. 19, 2021

(54) SYSTEMS AND METHODS TO IMPROVE INSTRUMENT GUIDANCE WITHIN AN INTRAVENOUS CATHETER ASSEMBLY

(71) Applicant: Becton, Dickinson and Company, Franklin Lakes, NJ (US)

(72) Inventors: Jonathan Karl Burkholz, Salt Lake City, UT (US); Bryan Bihlmaier, Provo, UT (US); Shaun Staley, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 299 days.

(21) Appl. No.: 16/037,274

(22) Filed: Jul. 17, 2018

(65) Prior Publication Data

US 2019/0022367 A1   Jan. 24, 2019

Related U.S. Application Data

(60) Provisional application No. 62/534,557, filed on Jul. 19, 2017.

(51) Int. Cl.
*A61M 39/10* (2006.01)
*A61M 39/00* (2006.01)
(Continued)

(52) U.S. Cl.
CPC ......... *A61M 39/10* (2013.01); *A61B 5/15003* (2013.01); *A61B 5/150396* (2013.01);
(Continued)

(58) Field of Classification Search
CPC ...... A61M 39/10; A61M 39/00; A61M 39/04; A61M 39/105; A61M 39/06;
(Continued)

(56) References Cited

U.S. PATENT DOCUMENTS 3,863,632 A * 2/1975 Schwartz .......... A61M 25/0606
   604/170.01
5,507,728 A * 4/1996 Erskine ............ A61M 25/0105
   604/159

(Continued)

FOREIGN PATENT DOCUMENTS

CN    103285450    9/2013
EP     2952220    12/2015
(Continued)

*Primary Examiner* — Bhisma Mehta
*Assistant Examiner* — James D Ponton
(74) *Attorney, Agent, or Firm* — Kirton & McConkie; Craig Metcalf; Kevin Stinger

(57) ABSTRACT

A catheter assembly and/or an introducer may include one or more features configured to guide a probe and/or a catheter distally through a septum. The catheter assembly may include a catheter adapter and the septum. The catheter adapter may include a distal end, a proximal end, and a lumen extending therebetween. In some embodiments, the septum may be disposed within the lumen. The septum may include a proximal surface that is tapered inwardly in a distal direction such that the proximal surface of the septum is configured to guide the probe and/or the catheter distally through the septum. The catheter assembly may be configured to receive an introducer, which may include an introducer element. A proximal end of the introducer element may include another proximal surface that is tapered inwardly in the distal direction such that the other proximal surface is configured to guide the probe or the catheter distally through the septum.

10 Claims, 11 Drawing Sheets

(51) Int. Cl.
  *A61M 39/04* (2006.01)
  *A61M 25/06* (2006.01)
  *A61M 39/06* (2006.01)
  *A61M 25/00* (2006.01)
  *A61M 5/32* (2006.01)
  *A61B 5/15* (2006.01)
  *A61M 39/16* (2006.01)

(52) U.S. Cl.
  CPC ....... *A61B 5/150992* (2013.01); *A61M 5/322* (2013.01); *A61M 5/3275* (2013.01); *A61M 25/0606* (2013.01); *A61M 25/0618* (2013.01); *A61M 39/00* (2013.01); *A61M 39/04* (2013.01); *A61M 39/105* (2013.01); *A61M 25/0023* (2013.01); *A61M 25/0097* (2013.01); *A61M 25/0631* (2013.01); *A61M 25/0637* (2013.01); *A61M 39/06* (2013.01); *A61M 39/162* (2013.01); *A61M 2039/0036* (2013.01); *A61M 2039/0072* (2013.01); *A61M 2039/062* (2013.01); *A61M 2039/066* (2013.01); *A61M 2039/1066* (2013.01); *A61M 2039/1072* (2013.01); *A61M 2039/1077* (2013.01)

(58) Field of Classification Search
  CPC .. A61M 39/162; A61M 5/322; A61M 5/3275; A61M 25/0606; A61M 25/0618; A61M 25/0023; A61M 25/0097; A61M 25/0631; A61M 25/0637; A61M 2039/0036; A61M 2039/0072; A61M 2039/062; A61M 2039/066; A61M 2039/1066; A61M 2039/1072; A61M 2039/1077; A61B 5/15003; A61B 5/150396; A61B 5/150992
  See application file for complete search history.

(56) References Cited

U.S. PATENT DOCUMENTS

| | | | |
|---|---|---|---|
| 5,695,474 A * | 12/1997 | Daugherty | A61M 5/3243 604/162 |
| 6,213,978 B1 * | 4/2001 | Voyten | A61M 25/0606 604/164.01 |
| 9,545,495 B2 * | 1/2017 | Goral | A61M 25/0015 |
| 9,895,524 B2 | 2/2018 | Lareau | |
| 2001/0053895 A1 * | 12/2001 | Vaillancourt | A61M 25/0606 604/243 |
| 2002/0045843 A1 * | 4/2002 | Barker | A61B 5/15003 600/585 |
| 2002/0177814 A1 | 11/2002 | Meng et al. | |
| 2006/0015086 A1 | 1/2006 | Rasmussen et al. | |
| 2006/0135962 A1 | 6/2006 | Kick et al. | |
| 2011/0160662 A1 * | 6/2011 | Stout | A61M 25/0097 604/122 |
| 2012/0197200 A1 | 8/2012 | Belson | |
| 2013/0090607 A1 | 4/2013 | McKinnon et al. | |
| 2013/0165867 A1 | 6/2013 | Isaacson et al. | |
| 2013/0310751 A1 | 11/2013 | Davis et al. | |
| 2014/0135703 A1 | 5/2014 | Yeh et al. | |
| 2014/0163516 A1 | 6/2014 | Lareau | |
| 2014/0350485 A1 | 11/2014 | Sonderegger et al. | |
| 2014/0364809 A1 | 12/2014 | Isaacson et al. | |
| 2015/0343179 A1 * | 12/2015 | Schumacher | A61M 25/0111 604/171 |
| 2015/0360005 A1 * | 12/2015 | Arellano Cabrera | A61M 25/0606 604/110 |
| 2016/0331937 A1 * | 11/2016 | Teoh | A61M 25/0097 |

FOREIGN PATENT DOCUMENTS

| | | |
|---|---|---|
| WO | 2017/074677 | 5/2017 |
| WO | 2018/067161 | 4/2018 |

\* cited by examiner

SYSTEMS AND METHODS TO IMPROVE INSTRUMENT GUIDANCE WITHIN AN INTRAVENOUS CATHETER ASSEMBLY

CROSS-REFERENCE TO RELATED APPLICATIONS

This application claims the benefit of U.S. Provisional Patent Application No. 62/534,557 filed Jul. 19, 2017, entitled SYSTEMS AND METHODS TO IMPROVE INSTRUMENT GUIDANCE WITHIN AN INTRAVENOUS CATHETER ASSEMBLY, of which is incorporated herein in its entirety.

BACKGROUND OF THE INVENTION

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous ("IV") catheter. As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal using a peripheral IV catheter may be difficult for several reasons, particularly when an indwelling time of the catheter is more than one day. For example, when the catheter is left inserted in the patient for a prolonged period of time, the catheter may be more susceptible to narrowing, collapse, kinking, blockage by debris (e.g., fibrin or platelet clots), and adhering of a tip of the catheter to the vasculature. Due to this, catheters may often be used for acquiring a blood sample at a time of catheter placement but are much less frequently used for acquiring a blood sample during the catheter dwell period. Therefore, when a blood sample is required, an additional needle stick may be needed to provide vein access for blood collection, which may be painful for the patient and result in higher material costs. Accordingly, there is a need for catheter systems and methods that facilitate placement of blood sample instruments, such as, for example, catheters, and probe instruments in the vasculature of the patient without additional needle sticks.

BRIEF SUMMARY OF THE INVENTION

The present application relates generally to instrument guidance within a catheter system, which may include a peripheral IV catheter system. In some embodiments, the catheter system may include a catheter assembly. In some embodiments, the catheter assembly may include one or more of the following: a catheter, a catheter adapter, a septum housing, and a septum.

In some embodiments, the catheter adapter may include a distal end, a proximal end, and a lumen extending therebetween. In some embodiments, the septum may be disposed within the lumen of the catheter adapter. In some embodiments, the septum may be at least partially disposed within the septum housing and configured to at least substantially seal the lumen of the catheter adapter. In some embodiments, the septum housing may prevent dislodgement or destabilization of the septum, thereby preventing leakage of fluid from the lumen of the catheter adapter.

In some embodiments, the catheter assembly may be part of a closed IV catheter system or a catheter system with an integrated extension tube, such as, for example, the Becton Dickinson NEXIVA™ Closed IV Catheter System, the Becton Dickinson NEXIVA™ DIFFUSICS™ Closed IV Catheter System, or the Becton Dickinson PEGASUS™ Safety Closed IV Catheter System. In these and other embodiments, a proximal end of the catheter adapter may include a first port and a second port. In these and other embodiments, the lumen of the catheter adapter may include a first lumen and/or a second lumen. In some embodiments, the first port may form the first lumen and/or the second port may form the second lumen. In some embodiments, the first and second lumens may join at a common lumen. In some embodiments, the first lumen may be generally aligned with the common lumen and/or the second port may include a side port. In some embodiments, the septum and/or the septum housing may be disposed in the first lumen.

In the closed IV catheter system, an introducer needle may be withdrawn through the catheter adapter after insertion of the catheter into vasculature of a patient. In the closed IV catheter system, when the introducer needle is withdrawn through the catheter adapter, the first lumen, which may correspond to a "needle channel," may be closed off by the septum from an external environment surrounding the catheter adapter. Thus, the septum may at least substantially seal the first port and prevent fluid from exiting the catheter adapter through the first port. In some embodiments, a fluid pathway of the catheter assembly during fluid infusion and/or blood withdrawal may extend through the second port and not the first port.

In some embodiments, the second lumen of the catheter adapter may be connectable to blood withdrawal or infusion means via an extension tube that may extend from the second port of the catheter adapter. In some embodiments, the septum and/or the septum housing may be disposed proximal to the second port of the catheter adapter. In some embodiments, the catheter assembly may be part of another type of catheter system, such as, for example, a non-integrated catheter system or a catheter system without the integrated extension tube.

In some embodiments, the instrument may include another catheter or a probe. In some embodiments, the instrument may include a variable diameter along a length of the instrument. In some embodiments, the instrument may be guided by one or more features of the catheter system, such as, for example, one or more tapered surfaces, to allow the instrument to access a fluid pathway of the catheter assembly and/or the vasculature of the patient. In some embodiments, one or more features of the catheter system may guide the instrument through the septum to access the fluid pathway. In some embodiments, by accessing the fluid pathway and/or the vasculature through the septum, insertion of the instrument through a long and tortuous path of an integrated extension set may be avoided.

In some embodiments, the septum may include a proximal surface that is tapered inwardly in a distal direction such that the proximal surface is configured to guide an instrument distally through the septum. In some embodiments, the septum may include a cavity. In some embodiments, a distal end of the cavity may include an annular protrusion, which may form the proximal surface of the septum. In some embodiments, the septum may include a slit disposed at or near a center of or within the annular protrusion. In some embodiments, the proximal surface of the septum may include an inner surface of the septum or a surface of the septum disposed towards the slit of the septum.

In some embodiments, the septum housing may include a proximal surface that is tapered inwardly in the distal direction such that the proximal surface of the septum housing is configured to guide the instrument distally through the septum. In some embodiments, the septum housing may include a distal end and a proximal end. In some embodiments, the septum may be disposed at least partially within the distal end of the septum housing. In some embodiments, the proximal end of the septum housing may include the proximal surface of the septum housing. In some embodiments, the septum housing may include a canister.

In some embodiments, the catheter system may include an extension or introducer, which may be configured to introduce the instrument into the catheter assembly. In some embodiments, the introducer may include an introducer element, which may be coupled with the proximal end of the catheter adapter. In some embodiments, a proximal end of the introducer element may include an opening being at least partially formed by a proximal and/or an inner surface. In some embodiments, the inner surface may be tapered inwardly in the distal direction such that the inner surface is configured to guide the instrument distally through the introducer element and into the proximal end of the catheter adapter.

In some embodiments, the proximal end of the introducer element may include a coupling mechanism. In some embodiments, a distal end of the introducer element may include a tube or tubular element. In some embodiments, in response to the introducer being coupled to the catheter adapter via the coupling mechanism, the tube may penetrate the septum and/or extend proximate a proximal face of septum, which may help guide the instrument within the catheter assembly. In some embodiments, a distal end of the tube may be blunt, which may prevent harm to the septum.

In some embodiments, the introducer may include a cover disposed over top or at least partially covering the tube. In some embodiments, the cover may contact the proximal face of the septum. In some embodiments, the cover may be elastomeric. In some embodiments, the cover may include a slit, which may facilitate penetration of the cover by the instrument. In some embodiments, the slit of the cover may be aligned with the slit of the septum. In some embodiments, the cover may include one or more antimicrobial agents. In some embodiments, the cover may be configured to seal the introducer from any fluid leakage through the septum when the septum is closed.

In some embodiments, the introducer may include a sheath or sleeve, which may be coupled to the introducer element. In some embodiments, the sleeve may surround the instrument, which may protect the instrument from the external environment surrounding the introducer. In some embodiments, the instrument may be at least partially disposed within the sleeve. In some embodiments, the instrument may be advanced to a position beyond a distal end of the sleeve when the sleeve is compressed or collapsed in the distal direction. In some embodiments, the introducer may include a grip, which may be coupled to a proximal end of the sleeve. In some embodiments, a clinician may move the grip distally to compress or collapse the sleeve in the distal direction and advance the instrument to the position beyond the distal end of the sleeve. In some embodiments, the coupling mechanism may be coupled to a particular port of the catheter adapter. In some embodiments, the fluid may be prevented by the septum from exiting the catheter adapter via the particular port. In some embodiments, the sleeve may be at least partially disposed in a housing, as will be described in further detail.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention. Moreover, the Figures may show simplified or partial views, and the dimensions of elements in the Figures may be exaggerated or otherwise not in proportion for clarity.

As used in the present disclosure, the terms "proximal" and "distal" may refer to the direction closer to and away from, respectively, a clinician who would place the catheter system into contact with a patient. Thus, for example, the end of the catheter system first touching the body of the patient would be the distal end, while the opposite end of the catheter system (e.g., the end of the device being manipulated by the clinician) would be the proximal end of the catheter system.

Figure 1A:
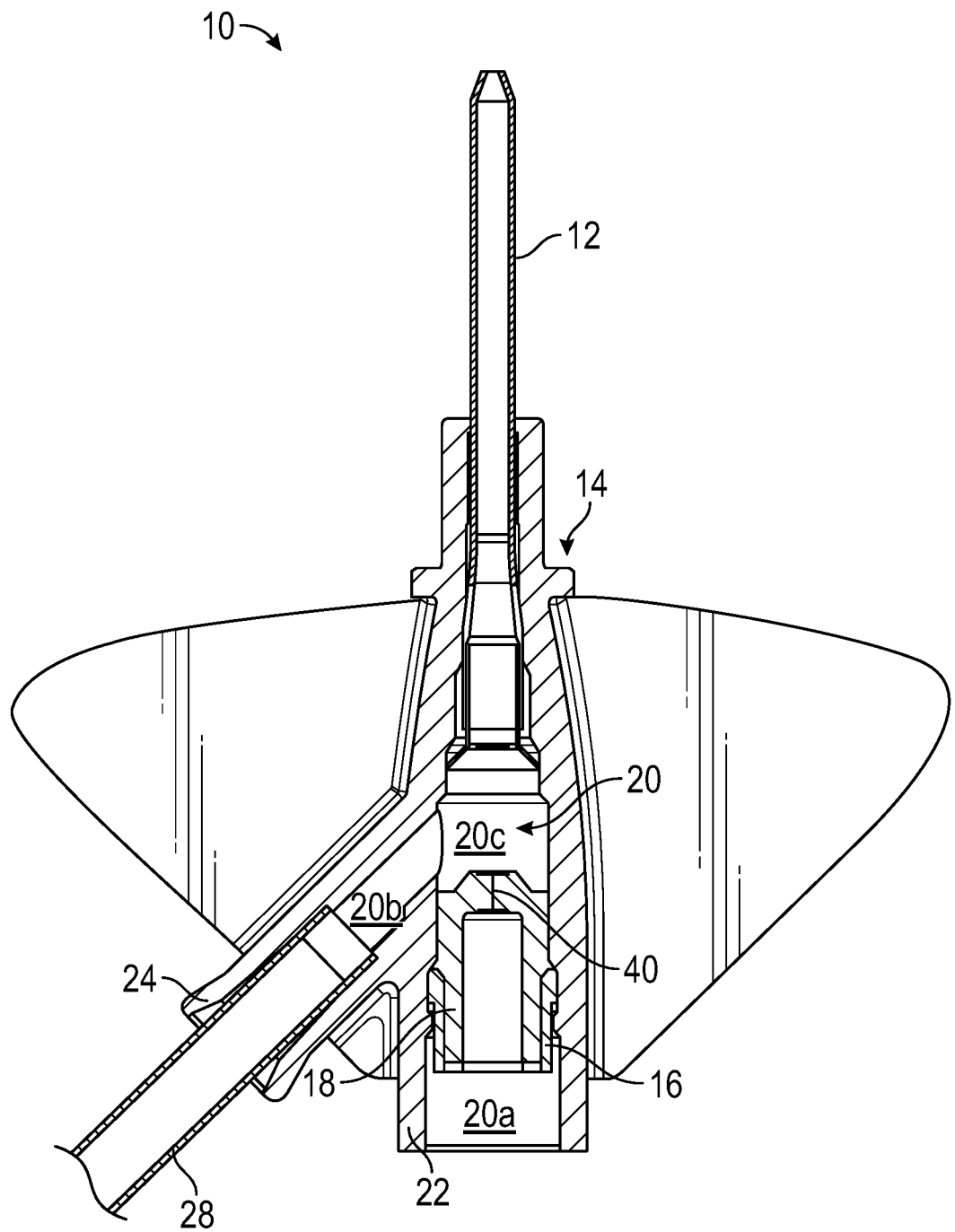
FIG. 1A is a cross-sectional top view of an example catheter assembly, according to some embodiments.
Figure 1B:
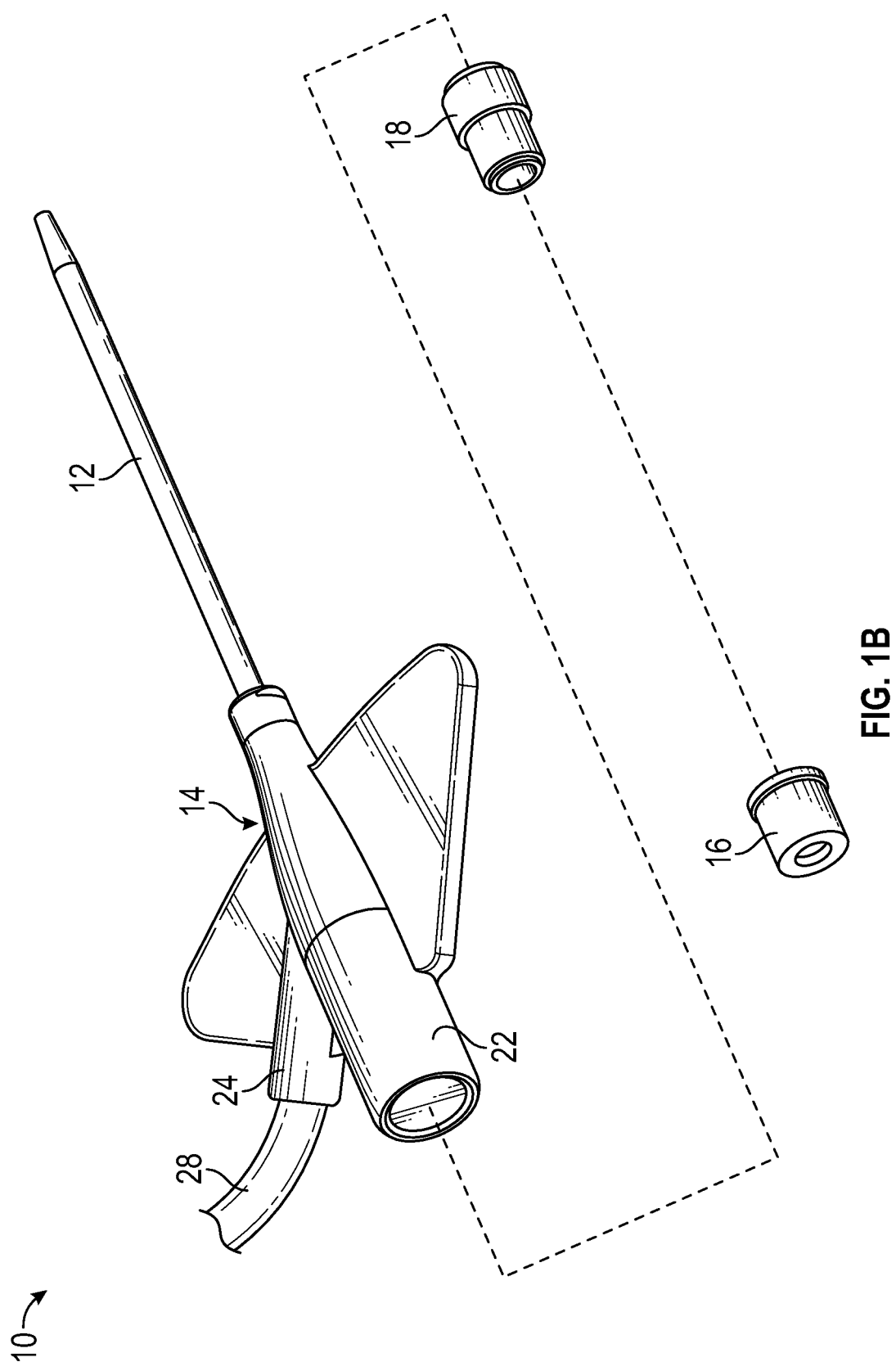
FIG. 1B is a partial exploded view of the catheter assembly of FIG. 1A, according to some embodiments.
Figure 1C:
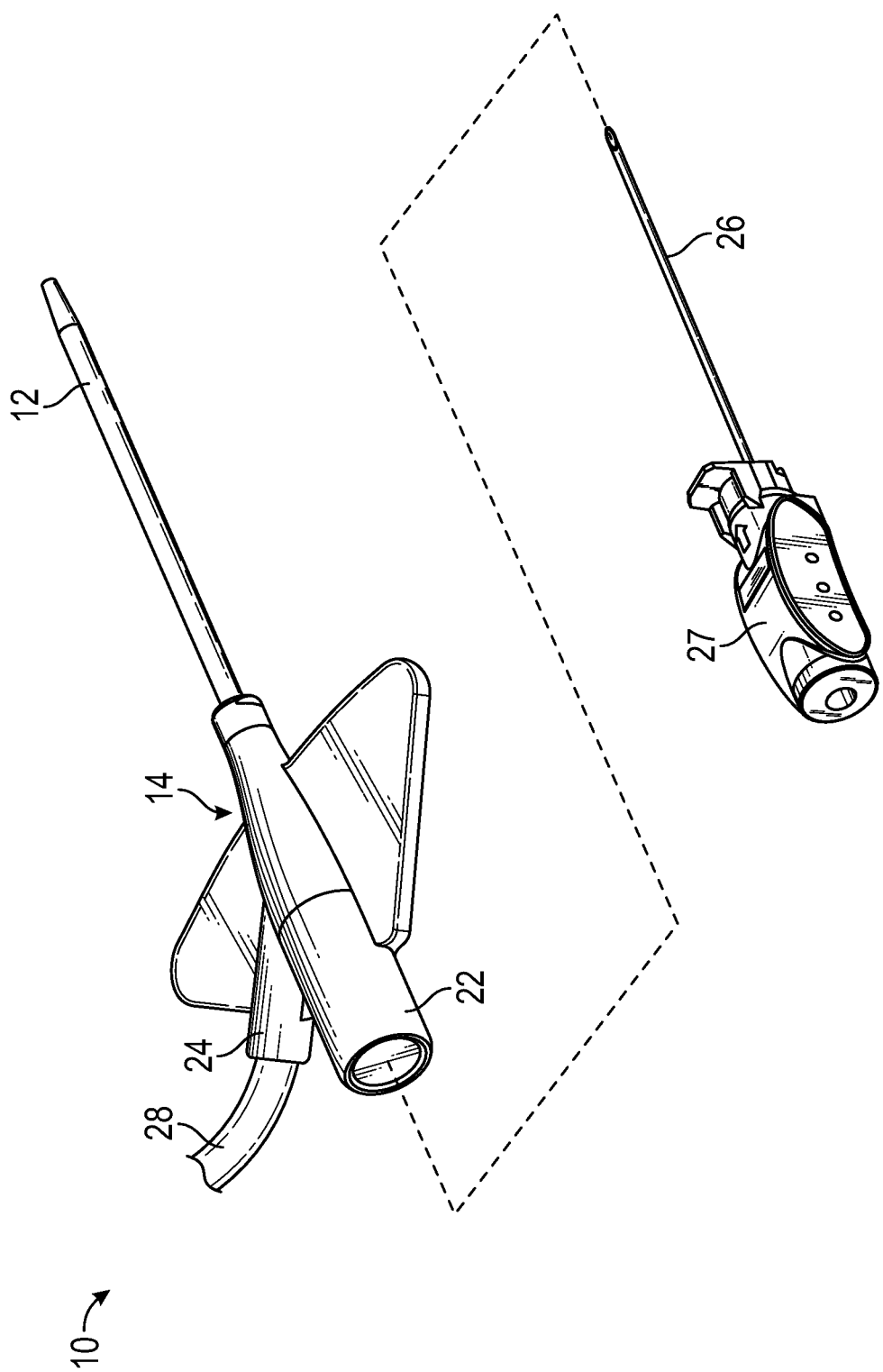
FIG. 1C is an upper perspective view of an example needle hub configured to be coupled with the catheter assembly of FIG. 1A, according to some embodiments.

The present application relates generally to instrument guidance within a catheter system, which may include a peripheral IV catheter system. Referring now to FIGS. 1A-1C, in some embodiments, the catheter system may include a catheter assembly 10. In some embodiments, the catheter assembly may include one or more of the following: a catheter 12, a catheter adapter 14, a septum housing 16, and a septum 18.

In some embodiments, the catheter adapter 14 may include a distal end, a proximal end, and a lumen 20 extending therebetween. In some embodiments, the septum 18 may be disposed within the lumen 20 of the catheter adapter 14. In some embodiments, the septum 18 may be at least partially disposed within the septum housing 16. In some embodiments, the septum housing 16 may prevent dislodgement or destabilization of the septum 18, thereby preventing leakage of fluid from the catheter adapter 14. In some embodiments, the septum 18 and the septum housing 16 may include or correspond to any of the septa 18 and septum housings 16, respectively, illustrated in any of the other Figures.

In some embodiments, the catheter assembly 10 may be part of a closed IV catheter system or catheter system with an integrated extension tube, such as, for example, the BD NEXIVA™ Closed IV Catheter System, the BD NEXIVA™ DIFFUSICS™ Closed IV Catheter System, or the Becton Dickinson PEGASUS™ Safety Closed IV Catheter System. In these and other embodiments, a proximal end of the catheter adapter 14 may include a first port 22 and a second port 24. In these and other embodiments, the lumen 20 of the catheter adapter 14 may include a first lumen 20a and/or a second lumen 20b. In some embodiments, the first port 22 may form the first lumen 20a and/or the second port 24 may form the second lumen 20b. In some embodiments, the first and second lumens 20a, 20b may join at a common lumen 20c. In some embodiments, the first lumen 20a may be generally aligned with the common lumen 20c and/or the second port 24 may include a side port. In some embodiments, the septum 18 and/or the septum housing 16 may be disposed in the first lumen 20a. In some embodiments, the septum 18 may be configured to at least substantially seal the first lumen 20a of the catheter adapter 14.

In the integrated or closed IV catheter system, an introducer needle 26 may be withdrawn through the catheter adapter 14 after insertion of the catheter 12 into the vasculature of a patient. In the integrated or closed IV catheter system, when the introducer needle 26 is withdrawn through the catheter adapter 14, the first lumen 20a, which may correspond to a "needle channel," may be closed off by the septum 18 from an external environment surrounding the catheter adapter 14. Thus, the septum 18 may prevent fluid from exiting the catheter adapter 14 through the first port 20a. In some embodiments, a fluid pathway of the catheter assembly 10 during fluid infusion and/or blood withdrawal may extend through the second port 20b and may not extend through the first port 20a and the septum 18.

In some embodiments, the second lumen 20b of the catheter adapter 14 may be connectable to blood withdrawal or infusion means via an extension tube 28 that may extend from the second port 20b of the catheter adapter 14. In some embodiments, the septum 18 and/or the septum housing 16 may be disposed proximal to the second port 20b of the catheter adapter 14.

It is understood that the catheter assembly 10 may include any number of ports. For example, the catheter assembly 10 may include a single port in which the septum 18 and/or the septum housing 16 may be disposed. In some embodiments, the catheter assembly 10 may include the first port 20a, the second port 20b, and one or more additional ports. In some embodiments, fluid may be prevented by the septum 18 from exiting the catheter adapter 14 via a particular port in which the septum 18 is disposed. In some embodiments, the catheter assembly 10 may be part of another type of catheter system, such as, for example, a non-integrated catheter system. In some embodiments, the extension tubing 28 and/or second port 20b may be absent. In these and other embodiments, the fluid pathway of the catheter adapter 14 may extend through the septum 18.

In some embodiments, the septum 18 may include a slit 40. In further detail, in some embodiments the septum 18, may be pre-slit prior to insertion of the introducer needle 26 through the septum 18 or the slit 40 may be formed when the introducer needle 26 is inserted through the septum 18. In some embodiments, the introducer needle 26 may be coupled to a needle hub 27, which may include a needle safety mechanism.

Figure 2A:
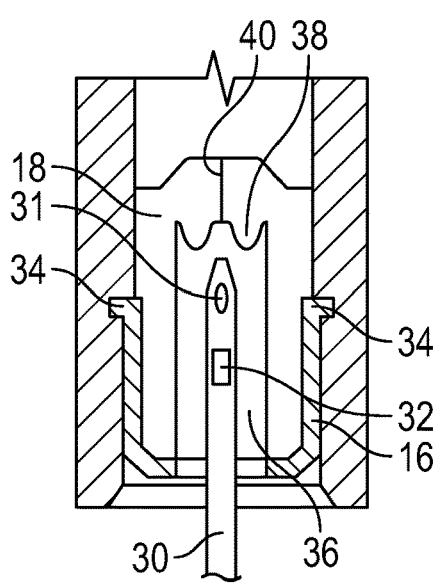
FIG. 2A is a cross-sectional view of an example septum that includes a guidance feature, according to some embodiments.
Figure 2B:
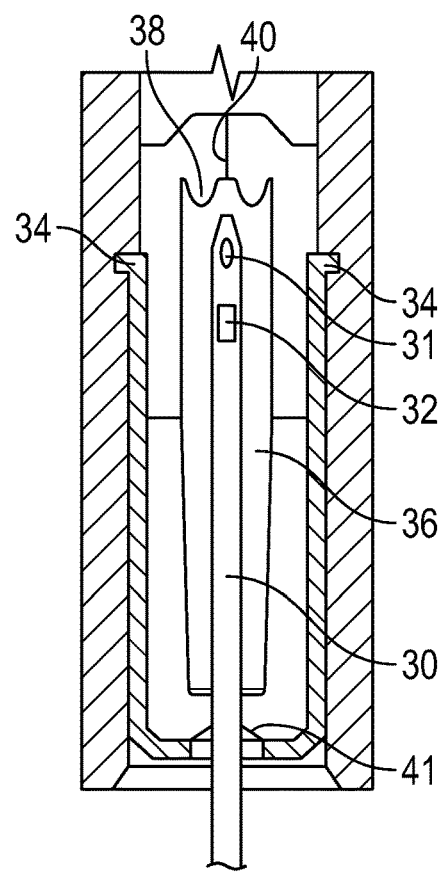
FIG. 2B is a cross-sectional view of another example septum that includes the guidance feature of FIG. 2A and another guidance feature, according to some embodiments.
Figure 2C:
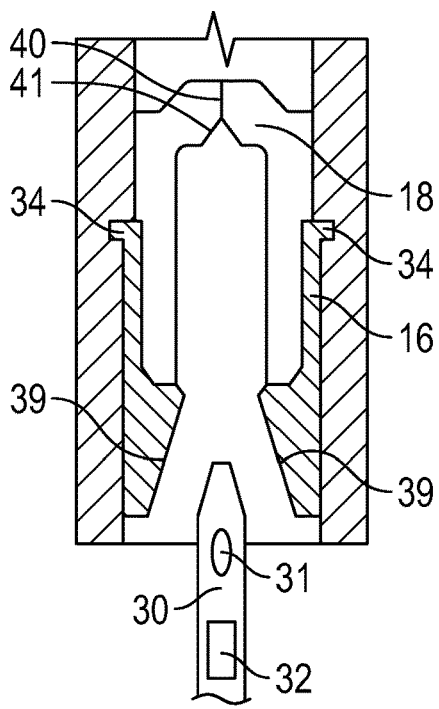
FIG. 2C is a cross-sectional view of a septum housing having another example guidance feature, according to some embodiments, according to some embodiments.
Figure 3A:
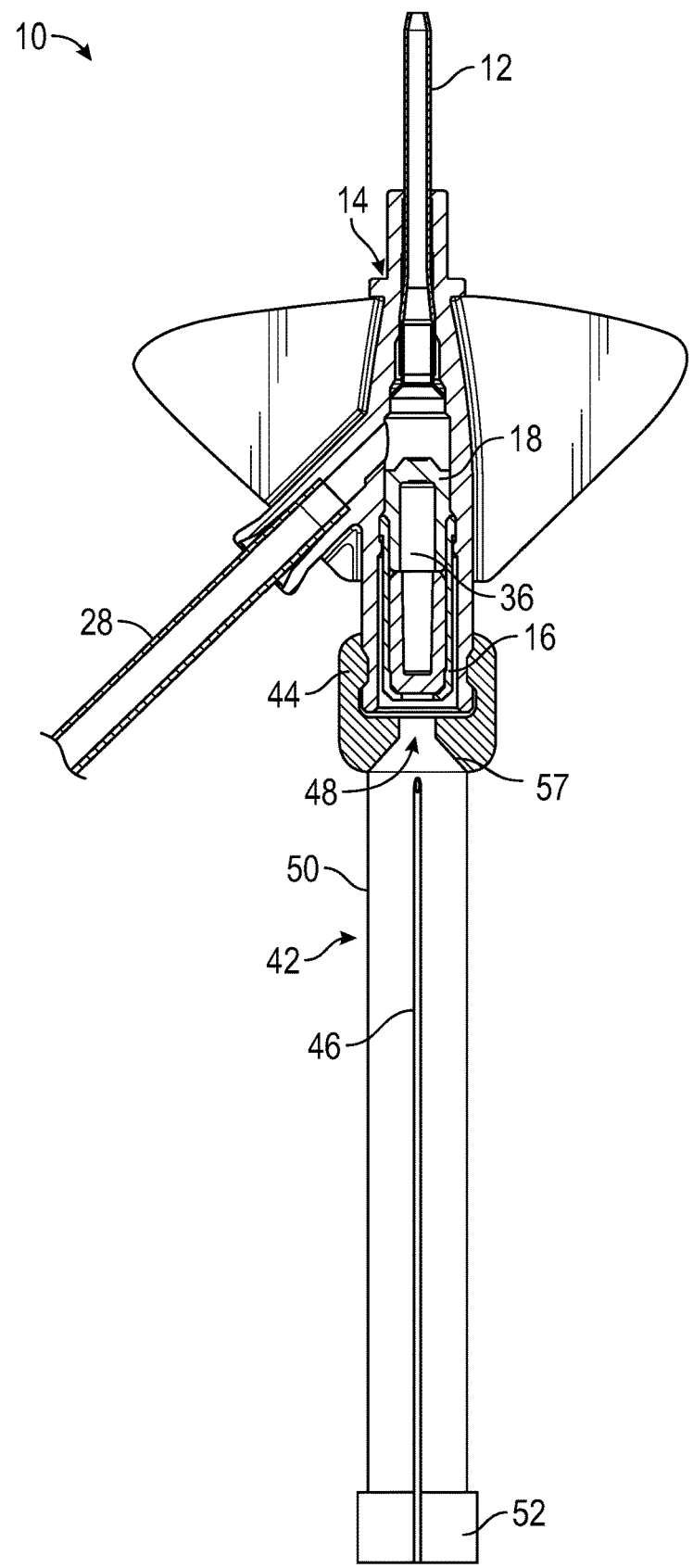
FIG. 3A is a cross-sectional view of an example introducer coupled to another example catheter assembly, illustrating the introducer in a first position, according to some embodiments.
Figure 3B:
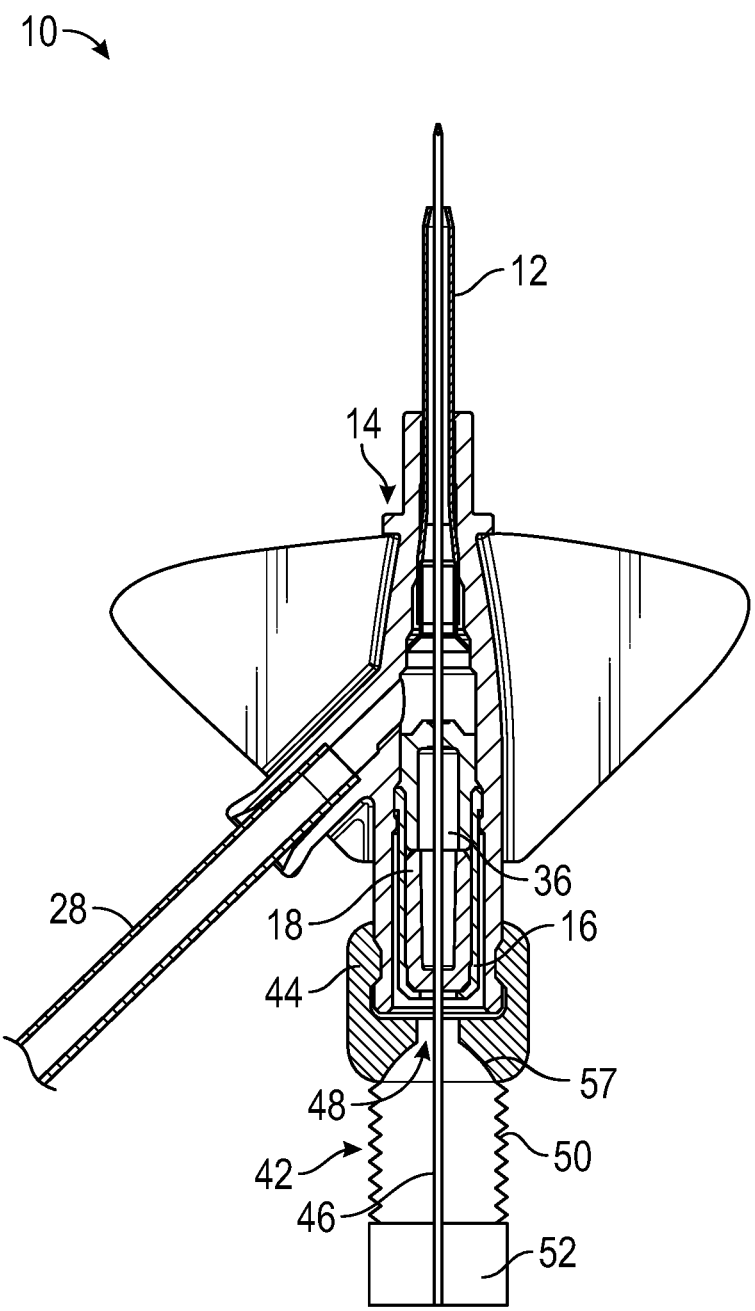
FIG. 3B is a cross-sectional view of the introducer of FIG. 3A, illustrating the introducer in a second position, according to some embodiments.

Referring now to FIGS. 2A-2C, in some embodiments, an instrument may include another catheter and/or a probe 30. An example of the probe 30 is illustrated in FIGS. 2A-2C. However, the probe 30 may be replaced with the other catheter, an example of which is illustrated in FIGS. 3A-3B. In some embodiments, the instrument may function as both the probe 30 and the other catheter. In some embodiments, the instrument may be useful for one or more of the following: diagnostics, blood sampling, monitoring, and one or more other purposes.

In some embodiments, the instrument may be guided by one or more features of the catheter system, such as, for example, one or more tapered surfaces, to allow the instrument to access the fluid pathway of the catheter assembly 10 and/or the vasculature of the patient. In some embodiments, the one or more features of the catheter system may include lead-in features and/or may guide the instrument through the septum 18 to access the fluid pathway of the catheter assembly 10. In some embodiments, by accessing the fluid pathway and/or the vasculature through the septum 18, insertion of the instrument through a long and tortuous path of an integrated extension set may be avoided.

In some embodiments, the other catheter may include a replacement catheter, which may be needleless. In some embodiments, the probe 30 may include one or more openings 31 and/or one or more sensors 32. In some embodiments, the openings 31 and/or the sensors 32 may be disposed towards a distal tip of the probe 30. In some embodiments, the openings 31 may serve as fluid inlets and/or outlets. In some embodiments, the sensors 32 may measure one or more parameters and/or detect one or more elements related to, for example, diagnostic information, blood chemistry, pressure, flow rate, drug identification, microbes, placement of an implantable stent, in-vein catheter tip stabilization feature, or other device, etc. In some embodiments, the one or more features may facilitate placement of a portion of the probe 30 that includes the sensors 32 within the fluid pathway of the catheter assembly 10 and/or the vasculature of the patient.

In some embodiments, the septum 18 may be a low-drag septum designed to reduce friction on the instrument passing through the septum 18, which may aid in threading the instrument through the septum 18. In some embodiments, the septum 18 may be configured to withstand high pressures within the catheter assembly 10. In some embodiments, the septum housing 16 and/or the septum 18 may be secured within the catheter adapter 14 in any number of ways. In some embodiments, the septum housing 16 may include one or more protrusions 34. In some embodiments, the one or more protrusions 34 may include a lip. In some embodiments, the septum housing 16 may be secured to an inner wall of the catheter adapter 14 by one or more of the following: an interference fit between the one or more protrusions 34 and the inner wall, a snap fit between the one or more protrusions 34 and the inner wall, bonding between the one or more protrusions 34 and the inner wall, and threading securing the one or more protrusions 34 to the inner wall. In some embodiments, the inner wall may include a groove or opening.

In some embodiments, the septum housing 16 may be resilient, and in response to the one or more protrusions 34 aligning with the groove or opening, the septum housing 16 may resiliently move outward to retain the one or more protrusions 34 within the groove or opening in the snap fit. In further detail, in some embodiments, in response to the septum housing 16 being inserted into the proximal end of the catheter adapter 14, the one or more protrusions 34 may be biased inwardly and/or in response to the one or more protrusions being further inserted into the proximal end and aligning with the groove or opening, the one or more protrusions 34 may move resiliently outward such that the one or more protrusions 34 are retained in the groove or opening.

In some embodiments, the bonding between the septum housing 16 and the inner wall and/or between the septum 18 and the inner wall may be disposed at various locations on the inner wall. In some embodiments, one or more of the following: adhesive bonding, chemical bonding, ultrasonic welding, and laser welding, may be disposed on all or some surfaces of the inner wall and/or the septum 18 that are in contact. Additionally or alternatively, one or more of the following: adhesive bonding, chemical bonding, ultrasonic welding, and laser welding, may be disposed on all or some surfaces of the inner wall and/or the septum housing 16 that are in contact.

In some embodiments, the septum 18 and/or the septum housing 16 may be retained within the catheter adapter 14 without requiring a mechanical or interference interface with the septum housing 16. For example, the proximal end of the catheter adapter 14 may abut and extend over a portion of a surface area of a proximal face of the septum 18 and/or the septum housing 16, thereby retaining the septum 18 and/or the septum housing 16 within the catheter adapter 14. Thus, the catheter adapter 14 may prevent the septum 18 and/or septum housing 16 from moving proximally within the catheter adapter 14 due to a wall at the proximal end of the catheter adapter 14 that abuts and thereby partially blocks the proximal end of the catheter adapter 14.

Referring now to FIGS. 2A-2B, in some embodiments, the septum 18 may include one or more guiding features that may facilitate guidance of the instrument distally through the septum 18. As an example, in some embodiments, the septum 18 may include an proximal surface that is tapered inwardly in a distal direction such that the proximal surface of the septum 18 is configured to guide the instrument distally through the septum 18. In some embodiments, the proximal surface of the septum 18 may be funnel-shaped or conical-shaped. In some embodiments, the septum 18 may include a cavity 36. In some embodiments, a distal end of the cavity 36 may include the proximal surface of the septum 18. In some embodiments, a slit 40 of the septum 18 may be disposed at or near a center of the proximal surface. In some embodiments, the distal end of the cavity 36 may include an annular protrusion 38, which may form the proximal surface of the septum 18. In some embodiments, the slit 40 may be disposed at or near a center of the annular protrusion 38. In some embodiments, the one or more guiding features of the septum 18 may include ribs, protrusions, grooves, or other guiding features that may facilitate direction of the instrument. In some embodiments, the proximal surface of the septum 18 may include the one or more guiding features. In some embodiments, guiding the instrument may include contacting the one or more guiding features.

In some embodiments, the one or more guiding features of the septum 18 may be disposed at a proximal end of the septum 18. For example, the proximal surface of the septum 18 may be disposed at a proximal end of the septum 18. FIG. 2B illustrates the proximal surface disposed at the proximal end of the septum and the proximal surface as a funnel-shape 41, for example.

Figure 2D:
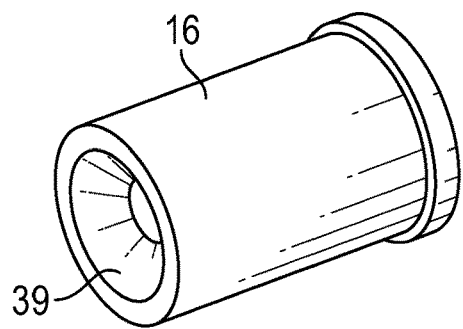
FIG. 2D is an upper perspective view of the septum housing of FIG. 2C, according to some embodiments.

Referring now to FIGS. 2C-2D, in some embodiments, the septum housing 16 may include one or more guiding features that may facilitate guidance of the instrument distally through the septum 18 and/or the septum housing 16. As an example, in some embodiments, the septum housing 16 may include a proximal surface 39 that is tapered inwardly in the distal direction such that the proximal surface 39 is configured to guide the instrument distally through the septum 18. In some embodiments, the proximal surface 39 may be funnel-shaped or conical-shaped. In some embodiments, the septum housing 16 may include a distal end and a proximal end. In some embodiments, the septum 18 may be at least partially disposed within the distal end of the septum housing 16. In some embodiments, the proximal end of the septum housing 16 may include the proximal surface 39. In some embodiments, the septum housing 16 may include a canister, as illustrated, for example, in FIG. 2D.

In some embodiments, the one or more guiding features of the septum housing 16 may include ribs, protrusions, grooves, or other guiding features that may facilitate direction of the instrument. In some embodiments, the proximal surface of the septum housing 16 may include the guiding features. The proximal surface of the septum 18 illustrated in FIG. 2C illustrates the funnel-shape 41, as an example proximal surface. In some embodiments, a particular port of the catheter adapter 14 may include the one or more guiding features of the septum housing 16 and/or the septum housing 16 may be integrally formed with the particular port of the catheter adapter 14.

Referring now to FIGS. 3A-3B, in some embodiments, the catheter system may include an introducer 42, which may be configured to introduce the instrument into the catheter assembly 10. In some embodiments, the instrument may include another catheter 46, as illustrated, for example, in FIGS. 3A-3B. However, the catheter 46 may be replaced with the probe 30, an example of which is illustrated in FIGS. 2A-2C. In some embodiments, the instrument may function as both the probe 30 and the other catheter 46, including elements of both the probe 30 and the other catheter 46.

In some embodiments, the introducer 42 may include an introducer element 44, which may be coupled with the proximal end of the catheter adapter 14. In some embodiments, the introducer element 44 may include one or more guiding features that may facilitate guidance of the instrument distally through the septum. As an example, in some embodiments, a proximal end of the introducer element 44 may include an opening 48 at least partially formed by a proximal and/or inner surface 57, which may be tapered inwardly in the distal direction such that the inner surface 57 is configured to guide the instrument distally through the introducer element 44 and through the slit 40 of the septum 18. In some embodiments, the inner surface 57 may be conical-shaped or funnel-shaped, as illustrated, for example, in FIG. 3A. In some embodiments, the inner surface 57 may include one or more ribs, protrusions, grooves, or other guiding features that may facilitate direction of the instrument.

In some embodiments, the introducer element 44 may include one or more coupling mechanisms that may facilitate coupling between the proximal end of the catheter adapter 14 and the introducer element 44, which may prevent fluid leakage and/or contamination of the fluid pathway when the instrument is inserted within the catheter assembly 14. In further detail, in some embodiments, the introducer element 44 may be coupled with the proximal end of the catheter adapter 14 in any number of ways, such as, for example, snap-fit, threads, press-fit, interference-fit, or another suitable means. In some embodiments, a particular coupling mechanism of the introducer element 44 may be coupled to a particular port of the catheter adapter. As illustrated in FIGS. 3A-3B, in some embodiments, one or more protrusions may snap into one or more recesses of the catheter adapter 14.

In some embodiments, the catheter adapter 14 and/or the introducer element 44 may be monolithically formed as a single piece. In some embodiments, the instrument may be coupled with the introducer element 44. In other embodiments, the instrument may not be coupled with the introducer element 44.

In some embodiments, the introducer 42 may include a sheath or sleeve 50, which may be coupled to the introducer element 44. In some embodiments, the sleeve 50 may surround the instrument. In these and other embodiments, the sleeve 50 may shield the instrument from contaminants and/or isolate any blood or other fluids that may remain on the instrument after accessing the fluid pathway of the catheter assembly 10. In these and other embodiments, the sleeve 50 may protect the instrument from the external environment surrounding the introducer 42.

In some embodiments, the instrument may be at least partially disposed within the sleeve 50. In some embodiments, the sleeve 50 may constructed of a flexible and/or compliant material. In some embodiments, the sleeve 50 may be axially-collapsible or axially-compressible. In further detail, in some embodiments, the instrument may be advanced to a position beyond a distal end of the sleeve 50 when the sleeve is collapsed or compressed in the distal direction. In some embodiments, the introducer 42 may include a handle or grip 52, which may be coupled to a proximal end of the sleeve 50. In some embodiments, the clinician may move the grip 52 distally to collapse or compress the sleeve 50 in the distal direction and advance the instrument to the position beyond the distal end of the sleeve 50.

In some embodiments, various types of sleeves 50 may be used. In some embodiments, the introducer 42 may include a housing (not illustrated), which may be coupled with the introducer element 44. In some embodiments, the housing may include one or more components, such as, for example, concentric barrels. In some embodiments, at least a portion of the housing may be axially-collapsible or axially-compressible. For example, a first concentric barrel may be advanced into a second concentric barrel.

In some embodiments, the sleeve 50 may be at least partially disposed within the housing, which may be rigid or semi-rigid. An example housing is described in U.S. Provisional Patent Application. No. 62/534,552, filed Jul. 19, 2017, entitled "Extension Housing a Probe or Intravenous Catheter," which is hereby incorporated by reference in its entirety. In some embodiments, the housing may include a slot. In some embodiments, a tab or an adapter may be coupled with the proximal end of the instrument or near the proximal end of the instrument. In some embodiments, the tab or the adapter may be configured to move along the slot from a proximal position to a distal position. In some embodiments, in response to movement of the adapter from the proximal position to the distal position, the instrument may be advanced beyond the distal end of the sleeve 50 and/or the housing. In some embodiments, the adapter may include a cavity configured to receive a syringe or blood collection tube and/or a cannula configured to puncture a septum of the syringe and/or the blood collection tube. An example slot and example adapter is described in U.S. Provisional Patent Application. No. 62/534,552, filed Jul. 19, 2017, entitled "Extension Housing a Probe or Intravenous Catheter."

As mentioned, in some embodiments, at least a portion of the housing may be axially-collapsible or axially-compressible. For example, the housing may include one or more collapsing and/or telescoping barrels. Additionally or alternatively, the housing may include the slot. In some embodiments, a first concentric barrel may be advanced into a second concentric barrel. In some embodiments, at least a portion of the first concentric barrel and/or the second concentric barrel may be collapsible.

In some embodiments, the introducer 42 may not include the sleeve 50 and/or the grip 52. In these and other embodiments, the introducer element 44 may have an extended length such that a portion of the introducer element 44 protrudes from underneath a dressing used to cover an insertion site of the catheter 12, facilitating easy access to the septum 18 and/or supporting the instrument.

In some embodiments, the introducer element 44, the grip 52, or another portion of the introducer 42 may be connected to a luer fitting, Becton Dickinson LUER-LOK™ Access Device, or another device for blood collection and/or monitoring. In some embodiments, a fluid pathway of the introducer 42 may extend through the grip 52. In some embodiments, the introducer element 44, the grip 52, or another portion of the introducer 42 may be connected to a monitoring interface and/or monitoring equipment.

Figure 3C:
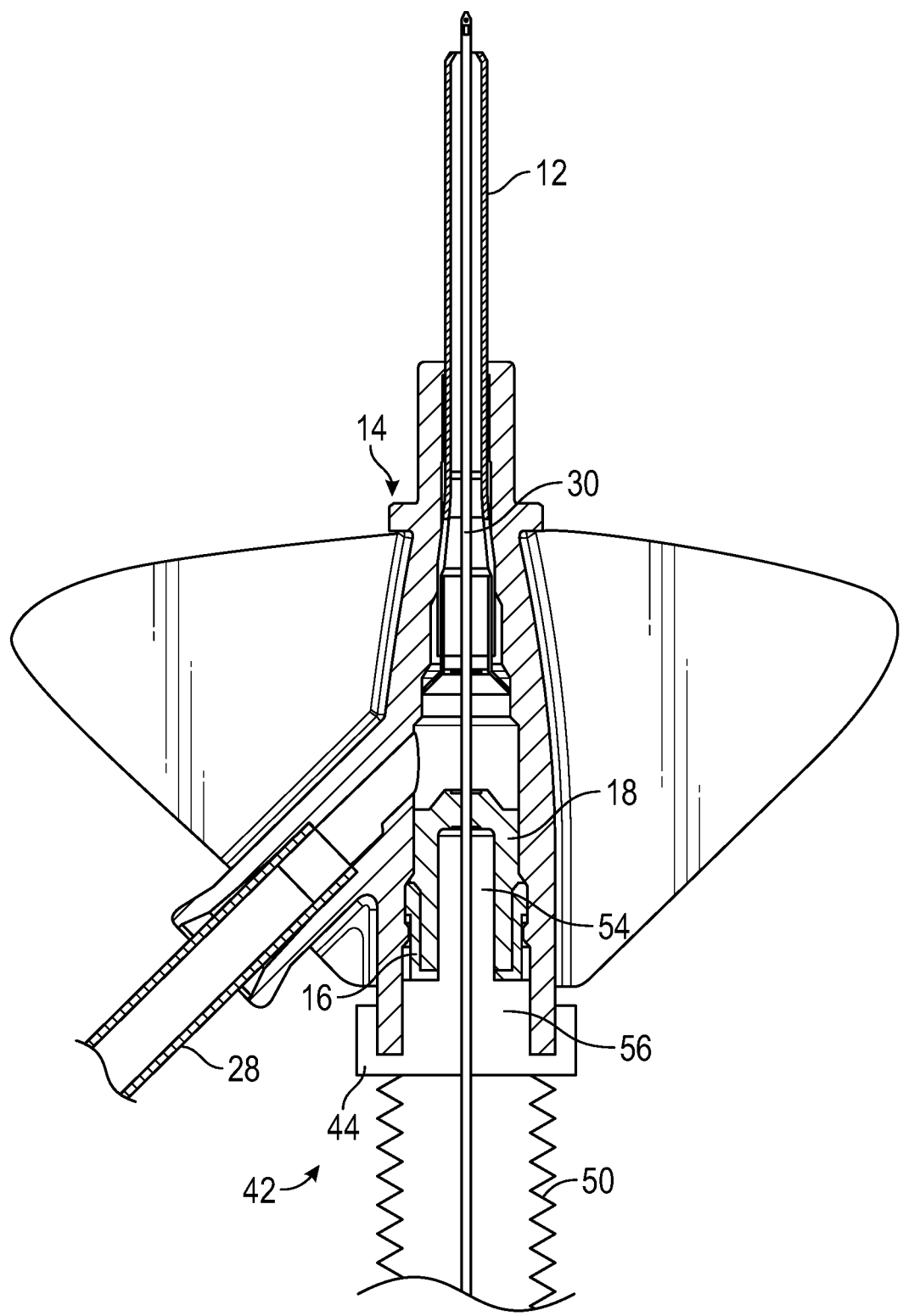
FIG. 3C is a cross-sectional view of another example introducer, illustrating the introducer in the second position, according to some embodiments.

Referring now to FIG. 3C, in some embodiments, the introducer element 44 may include a coupling mechanism. In some embodiments, a proximal end of the introducer element 44 may include the coupling mechanism. In some embodiments, a distal end of the introducer element may include a tube 54. In some embodiments, the coupling mechanism may be disposed proximal to the tube 54. In some embodiments, in response to the introducer 42 being coupled to the catheter adapter 14 via the coupling mechanism of the introducer element 44, the tube 54 may be disposed within the cavity 36 and/or proximate a proximal face of the septum 18. In these and other embodiments, the tube 54 may not penetrate the septum 18. In these and other embodiments, the tube 54 may contact the proximal face of the septum 18 proximate the slit 40. In some embodiments, the proximal face may be disposed within the cavity 36, although in some embodiments, the septum 18 may not include the cavity 36 and/or first and second proximally-extending arms forming the cavity 36. In some embodiments, a width of the tube 54 may be approximately equal to a width of the cavity 36. In some embodiments, a distal end of the tube 54 may be blunt, which may prevent harm to the septum 18. In some embodiments, the tube 54 may extend from a base 56 portion of the introducer element 44. FIG. 3C illustrates the probe 30, which may be replaced with the other catheter 46, as previously mentioned.

Figure 3D:
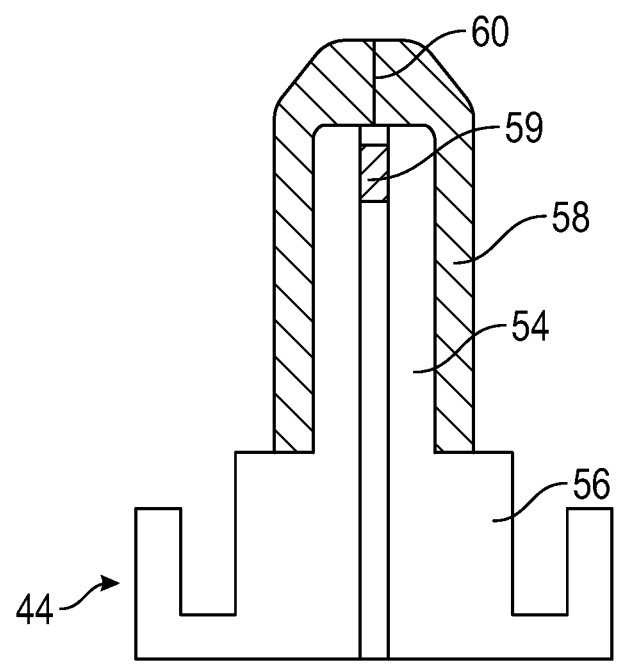
FIG. 3D is a cross-sectional view of an example cover disposed on an example introducer element, according to some embodiments.

Referring now to FIG. 3D, in some embodiments, the introducer element 44 may include a fluid seal, which may prevent fluid from entering a distal opening of the tube 54. For example, the introducer element 44 may include a cover 58, which may be configured to be penetrated by the instrument and provide a seal between the septum 18 and the introducer element 44. In some embodiments, the cover 58 disposed over top or at least partially covering the tube 54. In some embodiments, the cover 58 may cover the distal opening of the tube 54. In some embodiments, the cover 58 may be elastomeric and compliant. In some embodiments, the cover 58 may include a slit 60, which may facilitate penetration of the cover 58 by the instrument. In some embodiments, the cover 58 may include one or more antimicrobial agents. In some embodiments, the cover 58 may facilitate a fluid seal against the proximal face of the septum 18.

In some embodiments, the introducer 42 may include at least one valve 59, which may provide a seal that is penetrated by the instrument. In some embodiments, the valve 59 may include a slit. The valve 59 of the introducer 42 may be disposed at any number of locations to prevent fluid from the catheter assembly 10 from entering all or a portion of the introducer 42 and/or exiting the proximal end of the introducer. An example valve 59 is illustrated in FIG. 3D. In some embodiments, the introducer 42 may include the valve 59 and/or the cover 58. In some embodiments, when the introducer 42 does not penetrate the septum 18, such as, for example, in FIG. 3C, the introducer 42 may not include the valve 59 and/or the cover 58.

In some embodiments, any of the components of the catheter system, including any component of the introducer 42 and/or any component of the catheter assembly 10, for example, may include one or more antimicrobial agents, such as for example, an antimicrobial coating antimicrobial lubricant, etc. In some embodiments, the antimicrobial agents may reduce a risk of contamination of a fluid pathway of the catheter system.

Figure 4A:
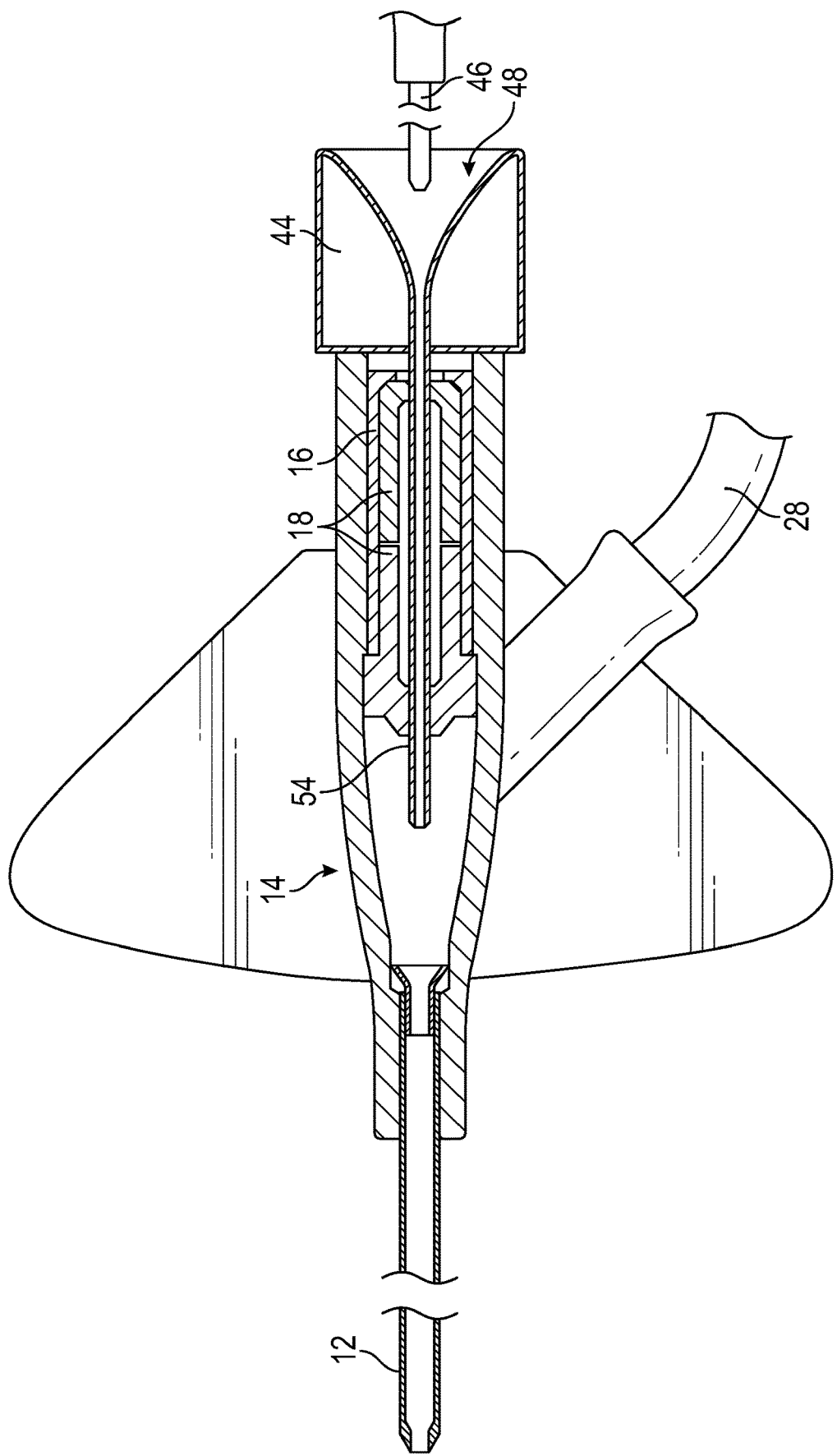
FIG. 4A is a cross-sectional view of another example introducer, according to some embodiments.
Figure 4B:
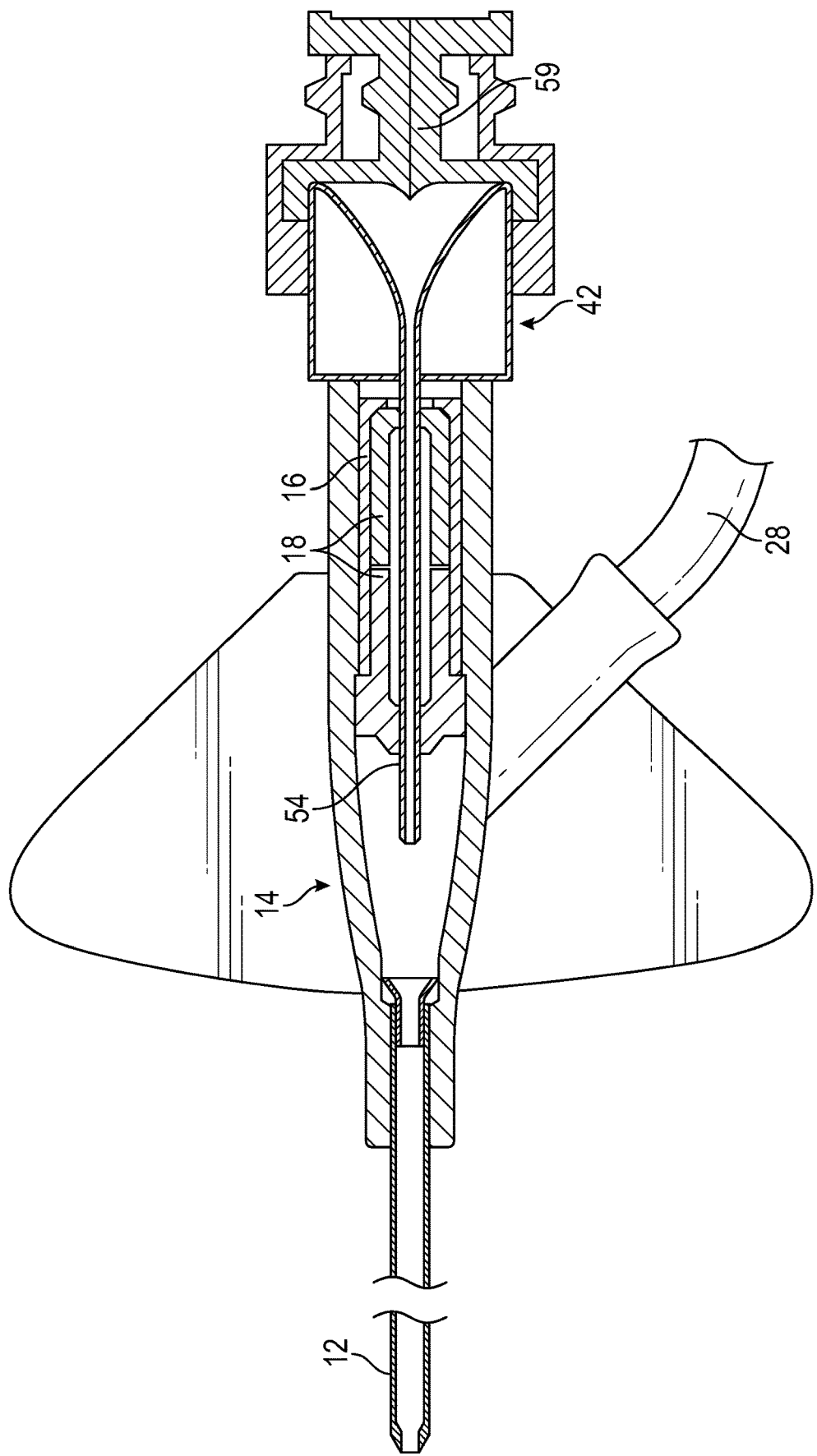
FIG. 4B is a cross-sectional view of the introducer of FIG. 4A, according to some embodiments.

Referring now to FIGS. 4A-4B, in some embodiments, in response to the introducer 42 being coupled to the catheter adapter 14 via the coupling mechanism of the introducer element 44, the tube 54 may penetrate the septum 18. In these and other embodiments, fluid within the cavity 36 of the septum 18 may be reduced and/or a compressive axial load on the instrument may be decreased compared to when the instrument itself opens the septum 18. In some embodiments, a distal end of the tube 54 may be blunt, which may prevent harm to the septum 18. In some embodiments, the introducer 42 of FIGS. 4A-4B may include one or more of the sleeve 50, the grip 52, and one or more other components discussed with respect to FIGS. 1-3. FIG. 4 illustrates the catheter 46 prior to insertion within the introducer 44, according to some embodiments.

Another example valve 59 is illustrated in FIG. 4B. In some embodiments, the valve 59 may be disposed within a needleless connector. In some embodiments, the needleless connector may form a proximal end of the introducer element 44. In some embodiments, the valve 59 may be disposed within the catheter adapter 14 distal to the septum 18. In these embodiments, the tube 54 may penetrate the septum 18 but not the valve 59, which may be penetrated by the instrument. In some embodiments, the valve 59 may provide less resistance to the instrument than the septum 18.

Figure 5:
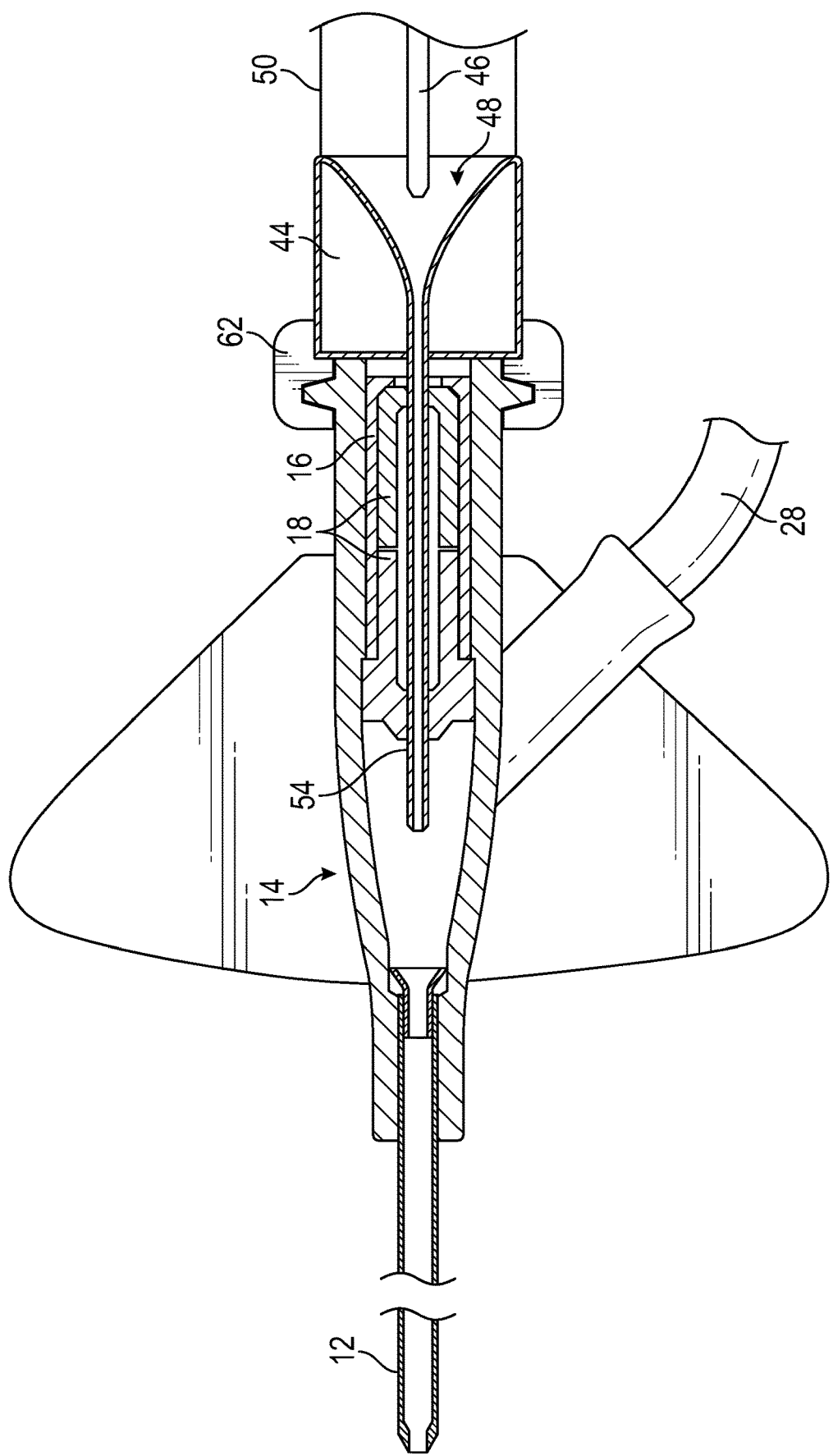
FIG. 5 is a cross-sectional view of the introducer of FIG. 4A, according to some embodiments.

Referring now to FIG. 5, as explained previously, in some embodiments, the introducer element 44 may be coupled with the proximal end of the catheter adapter 14 via any number of coupling mechanisms. For example, the introducer element 44 may be coupled with the proximal end of the catheter adapter via a snap-fit, threads, a press-fit, an interference-fit, etc. In some embodiments, the introducer 44 may include a connector 62, which may include the one or more coupling mechanisms, such as, for example, threads, as illustrated in FIG. 5. In some embodiments, the connector 62 may be coupled to the proximal end of catheter adapter 14 via the one or more coupling mechanisms. In some embodiments, the connector 62 may be removable from the introducer element 44 and/or the catheter adapter 14. In other embodiments, the connector 62 may be non-removable from or permanently coupled to the introducer element 44 and/or the catheter adapter 14. FIG. 5 illustrates the introducer element 44 coupled with the sleeve 50, according to some embodiments.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An introducer, comprising:
   an introducer element, comprising:
   a blunt tube, the blunt tube comprising a distal opening and configured for insertion within a catheter adapter, wherein the blunt tube comprises a first outer diameter;
   a base, wherein the base is configured to insert into the catheter adapter, wherein the base is generally cylindrical and comprises a second outer diameter that is greater than the first outer diameter, wherein the blunt tube extends distally from the base such that a stepped surface is formed between the blunt tube and the base;
   a pathway extending through the base, and the distal opening; and
   a compressible sleeve comprising a distal end and a proximal end;

a grip, wherein the distal end of the compressible sleeve is coupled to a proximal end of the introducer element and the proximal end of the compressible sleeve is coupled to the grip; and a catheter comprising a distal opening and configured for insertion through the introducer element and the catheter adapter, wherein in response to compression of the compressible sleeve in a distal direction, the distal opening of the catheter is advanced from a first position proximal to the distal end of the compressible sleeve to a second position that is distal to the introducer element.

2. The introducer of claim 1, wherein the proximal end of the introducer element further comprises a connector coupled to the base and configured to couple the introducer to the catheter adapter.

3. The introducer of claim 2, wherein the connector is configured to be coupled to a port of the catheter adapter.

4. The introducer of claim 1, wherein the introducer element further comprises a fluid seal configured to prevent fluid from entering the distal opening of the tube, wherein the fluid seal extends over the tube and contacts the stepped surface.

5. The introducer of claim 4, wherein the fluid seal comprises an elastomeric cover.

6. The introducer of claim 4, wherein the fluid seal comprises an antimicrobial agent.

7. The introducer of claim 4, wherein the introducer element further comprises a valve positioned within the pathway.

8. The introducer of claim 4, wherein the fluid seal comprises a slit by which the fluid seal may be penetrated.

9. The introducer of claim 1, wherein an inner surface of the distal opening of the blunt tube is tapered inwardly in a distal direction such that the inner surface is configured to guide the catheter distally through the blunt tube and into the catheter adapter.

10. The introducer of claim 1, wherein the distal opening of the catheter is disposed within the sleeve.

* * * * *